United States Patent
Thanas

(10) Patent No.: US 9,326,906 B2
(45) Date of Patent: May 3, 2016

(54) THERAPEUTIC PILLOW

(71) Applicant: Edwinia Thanas, Anderson, IN (US)

(72) Inventor: Edwinia Thanas, Anderson, IN (US)

(*) Notice: Subject to any disclaimer, the term of this patent is extended or adjusted under 35 U.S.C. 154(b) by 90 days.

(21) Appl. No.: 14/085,848

(22) Filed: Nov. 21, 2013

(65) Prior Publication Data

US 2014/0144451 A1 May 29, 2014

Related U.S. Application Data

(60) Provisional application No. 61/730,986, filed on Nov. 29, 2012.

(51) Int. Cl.
*A47C 20/00* (2006.01)
*A61G 7/075* (2006.01)
*A61G 7/07* (2006.01)
*A61F 5/01* (2006.01)
A61G 7/057 (2006.01)

(52) U.S. Cl.
CPC . *A61G 7/075* (2013.01); *A61F 5/01* (2013.01); *A61G 7/07* (2013.01); *A61G 7/072* (2013.01); *A61G 7/05738* (2013.01); *A61G 2200/325* (2013.01); *A61G 2210/10* (2013.01)

(58) Field of Classification Search
CPC .......... A47G 9/00; A47G 9/10; A61G 7/075; A61G 7/07; A61G 7/072; A61G 7/05738; A61G 2200/325; A61G 2210/10; A61F 5/01
USPC .......... 5/636, 652.1, 630–632, 645, 653, 652
See application file for complete search history.

(56) References Cited

U.S. PATENT DOCUMENTS

| | | |
|---|---|---|
| 4,598,701 A | 7/1986 | Schaefer |
| 4,896,660 A | 1/1990 | Scott |
| D317,840 S | 7/1991 | Jagdat |
| 5,359,739 A | 11/1994 | Rains et al. |
| 5,507,049 A | 4/1996 | Lane |
| 5,544,377 A | 8/1996 | Gostine |
| 5,824,013 A | 10/1998 | Allen |
| 6,065,166 A | 5/2000 | Sharrock et al. |
| 6,067,679 A | 5/2000 | Rice |
| 6,131,219 A | 10/2000 | Roberts |
| D447,376 S | 9/2001 | Krame |
| 6,449,788 B1 | 9/2002 | Nichols |
| 6,708,353 B2 | 3/2004 | Han |
| 6,932,781 B2 | 8/2005 | Itoi |
| 6,951,038 B1 | 10/2005 | Ganoe, Sr. |
| 7,017,215 B1 | 3/2006 | Singer et al. |
| 7,089,615 B1 | 8/2006 | Parimuha |
| 7,240,384 B2 | 7/2007 | DuDonis |
| 7,441,293 B1 | 10/2008 | Singer et al. |
| 7,563,236 B2 | 7/2009 | Kazmierczak et al. |

(Continued)

*Primary Examiner* — David E Sosnowski
(74) *Attorney, Agent, or Firm* — Maginot, Moore & Beck, LLP

(57) ABSTRACT

An orthopedic or therapeutic support pillow is provided for use by a patient to support an arm and shoulder while the patient is resting in a generally prone position on a resting surface. The pillow includes a back section for positioning and supporting the pillow on resting surface, the back section having a central memory foam section to adapt to the contour of the body of the patient. The pillow further includes a pair of side arms extending from the back section, each side arm including contoured areas and a plush thickness to support the body, arms, and shoulders. The back section includes shoulder support zones to engage and support the shoulders of the patient when reclining on the pillow.

13 Claims, 4 Drawing Sheets

(56) References Cited

U.S. PATENT DOCUMENTS

| | | |
|---|---|---|
| 7,634,829 B1 | 12/2009 | La Bar |
| 8,002,682 B2 | 8/2011 | Dye |
| D655,964 S | 3/2012 | Dror et al. |
| 8,739,336 B2 * | 6/2014 | Kiefer .......................... 5/652.1 |
| 2005/0172408 A1 | 8/2005 | Temple |
| 2008/0256714 A1 * | 10/2008 | Cubbage et al. .................. 5/656 |
| 2011/0252568 A1 | 10/2011 | Ramp |
| 2012/0006333 A1 | 1/2012 | Mason et al. |
| 2012/0131751 A1 | 5/2012 | Mahler |
| 2012/0186025 A1 * | 7/2012 | Kardos .......................... 5/655.9 |

* cited by examiner

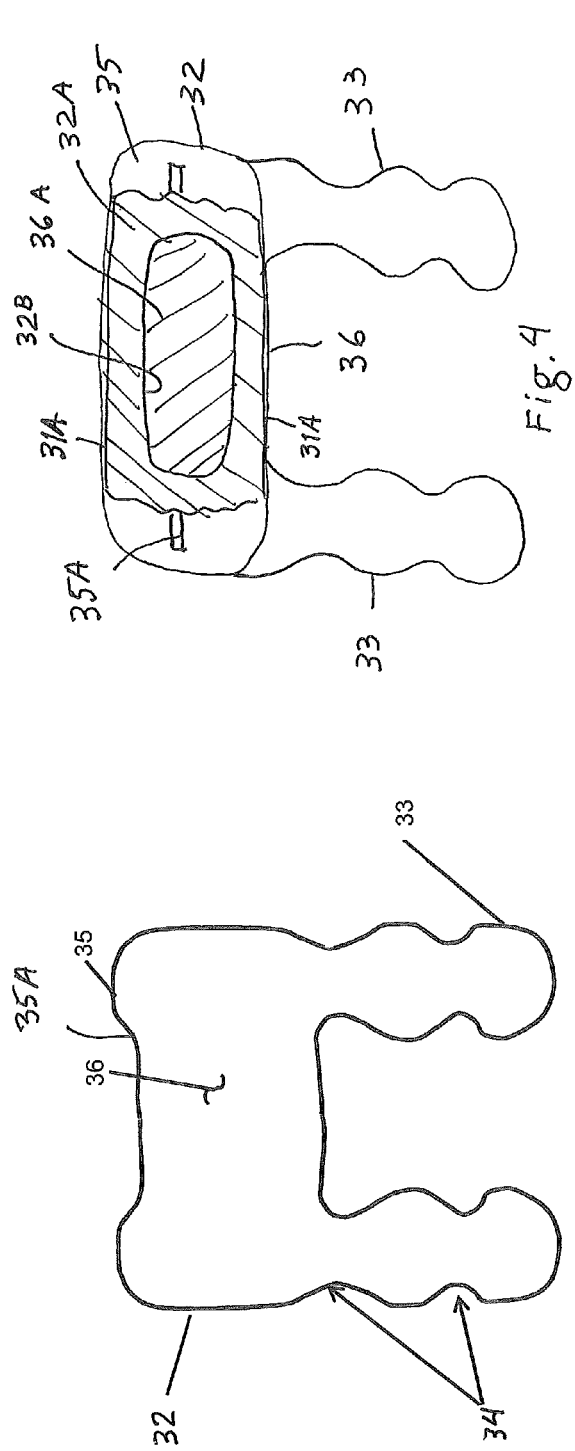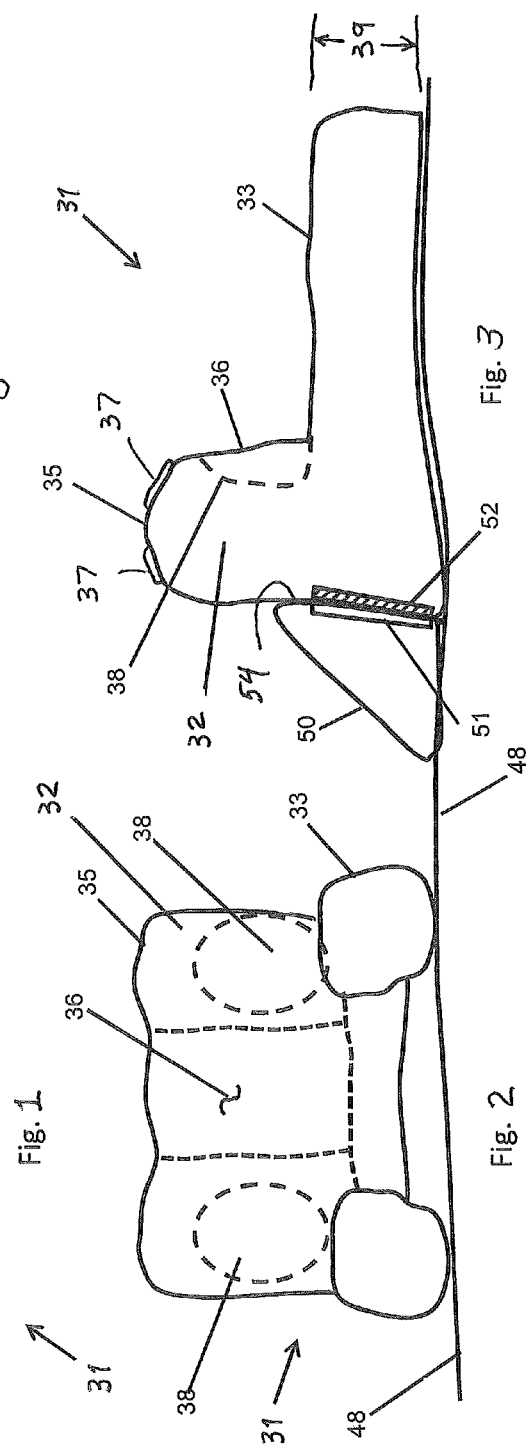

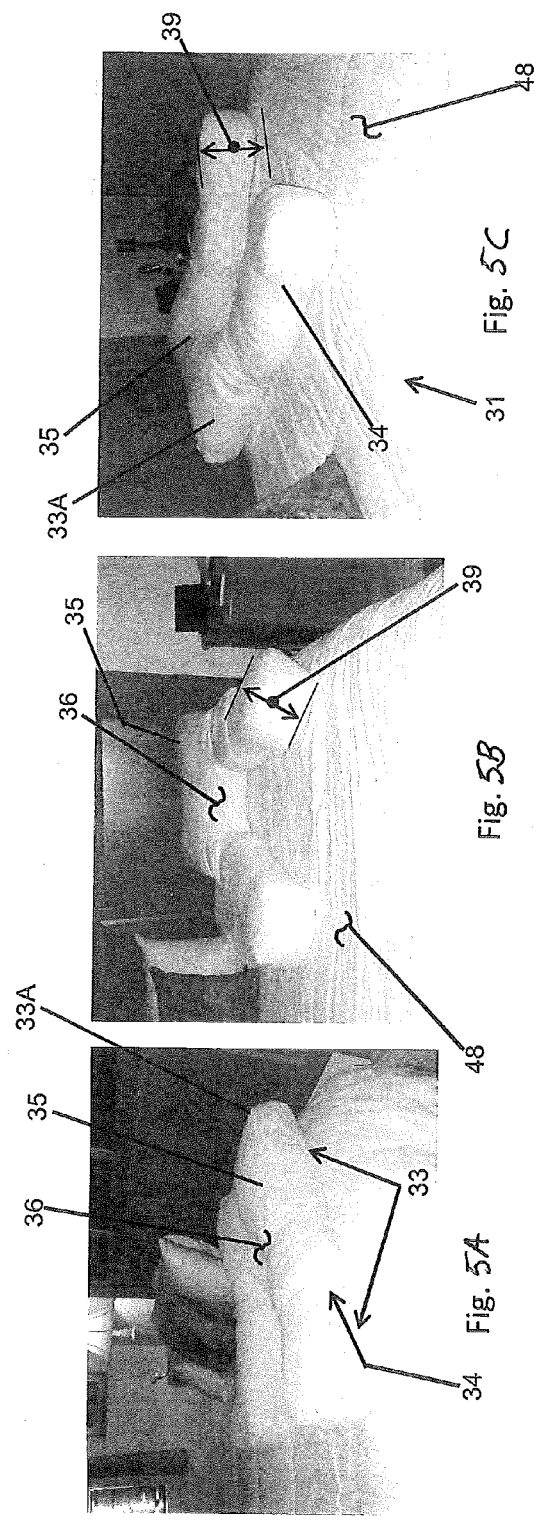
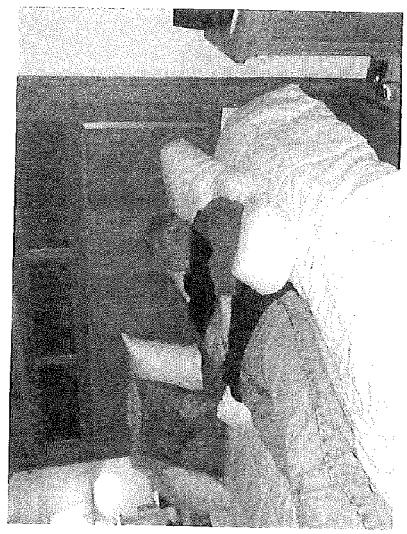

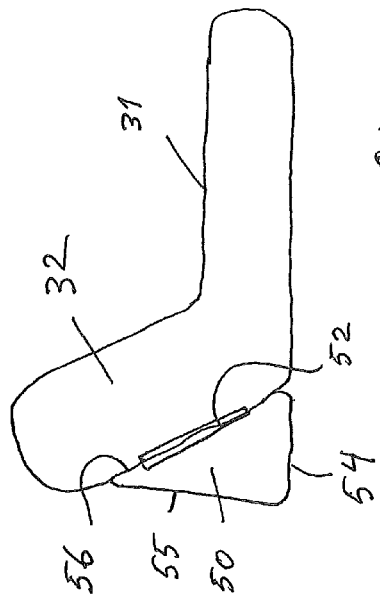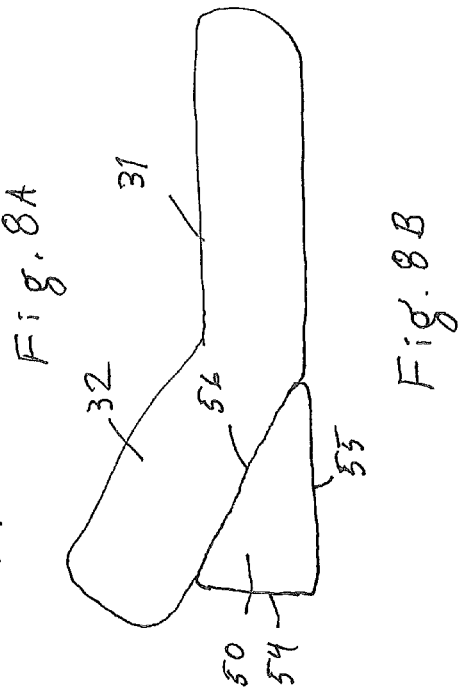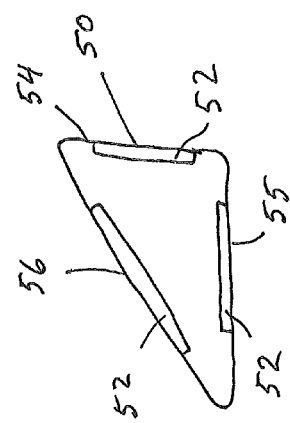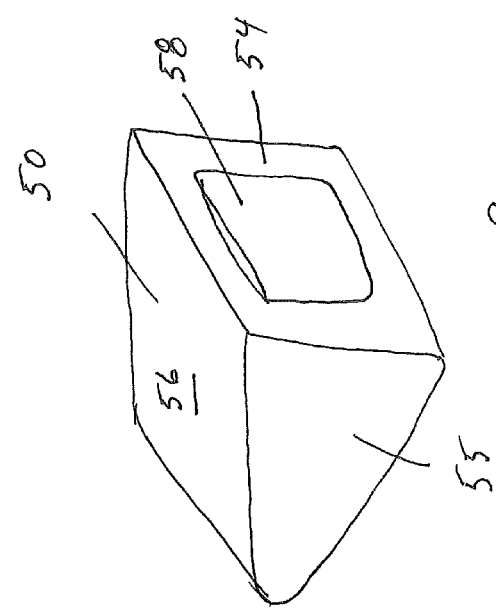

THERAPEUTIC PILLOW

CROSS-REFERENCE TO RELATED APPLICATIONS

The present application is a utility conversion and claims priority to provisional application No. 61/730,986, filed on Nov. 29, 2012, and entitled "Therapeutic Pillow Device Recovery Called an OrthoCradle," the entire disclosure of which is incorporated herein by reference.

FIELD OF INVENTION

The present disclosure related to multi-use orthopedic support pillow to be used by a patient to support an arms and shoulders of the patient while resting in a generally prone position.

This device is an orthopedic support pillow. In addition, the disclosure relates, in general, to a pillow, and, in particular, to an improved, pillow, or the like, having a malleable section of memory foam or the like and further sections of soft materials or foam surrounding the memory foam section to retain the specific shape as needed by a user/recovering patient. The applications and use anticipate post-operative recovery as well as preventive use for the device.

BACKGROUND

Generally, many musculoskeletal problems are related to the neck, upper extremities, and shoulders. For example, the "rotator cuff" is the group of muscles and their tendons that act to stabilize the shoulder. The rotator cuff muscles are important in shoulder movements and in maintaining shoulder joint stability. One of the most important things is to treat rotator cuff injury as soon as possible. The initial 48-72 hours are vital for a speedy recovery and complete. The conventional medical treatment as soon as injury occurs is rest, ice, compression, elevation, and referral.

The human shoulder has the greatest range of motion of any joint in the body. The shoulder joint comprises four muscles and their associated tendons that are referred to as the rotator cuff, which is surrounded by a bursa sac for accommodating movement of the tendons. Injury or trauma to the shoulder joint may comprise bursitis, tendonitis, arthritis, rotator cuff tears, calcification of the joint, subluxation (instability of the joint due to stretched or torn ligaments), dislocation, and/or actual breakage of the humerus, scapula, and/or clavicle bones.

A torn rotator cuff refers to damage to one of the four muscles that allow the arm to rotate at the shoulder. Rotator cuff tears can also affect the tendons that hold these muscles together. Generally, a torn rotator cuff is the result of repetitive use, but it can occur as a single traumatic injury. Rotator cuff tears are most common in active young people as well as older people who repeatedly perform activities with overhead motions, but they can occur in anyone. If one has a torn rotator cuff, he/she may experience muscle weakness, pain in the arm or shoulder, muscle wasting, or a crackling feeling when he/she moves their shoulder. The pain may get worse with time.

There are many treatments for rotator cuff tears, depending on the severity. In mild cases, the tear may repair itself over time, and rest, over-the-counter medication, and exercise may speed healing. Physical therapy, prescription medications, and steroids may be necessary in more serious cases, while severe cases of torn rotator cuff may require surgery. Surgery for torn rotator cuff ranges from smoothing of the tissues (debridement) to full tendon transfer (replacement of muscles or tendons). A combination of surgery and physical therapy often leads to a greater recovery.

Symptoms of torn rotator cuff include pain, an inability to move the shoulder, and swelling. A torn rotator cuff can be an acute (sudden) injury or a repetitive use (gradual) injury. Acute injuries may occur during strenuous activities, such as heavy lifting or sports, or may be due to an accident. More commonly, the rotator cuff will tear as a result of repetitive use, such as with frequent overhead lifting. In these cases, the muscles or tendons of the rotator cuff develop wear and tear over time. Athletes who frequently engage their rotator cuff, such as baseball players, have an increased risk of injury.

A simple, non-acute torn rotator cuff may heal on its own but can benefit from some amount of pain management, reducing inflammation, and physical therapy. If the tear is small and not excessively painful, treatments that include rest, a sling, and anti-inflammatory medications may be adequate for improving shoulder function. The more serious cases of torn rotator cuff may require surgery.

Treatment of shoulder joint injuries may comprise non-invasive techniques such as physical therapy and/or pain relief and anti-inflammatory medications. However, invasive techniques including shoulder replacement (shoulder arthroplasty), cortisone injections, and surgical repair of rotator cuff tears are also used in cases where a poor outcome from nonsurgical treatment is indicated, such as a long duration of symptoms and larger rotator cuff tears.

Deciding on when a torn rotator cuff will need surgical intervention is dependent on how the injury responds to other treatments. If other forms of non-surgical treatments prove to be ineffective even after a number of months, rotator cuff surgery may then be needed. Whether or not surgery is needed, bed rest and elevation of the retained arm are critical to the well-being and the recovery of the patient. Sleep devices to assist with shoulder or neck discomfort generally comprise the strategic placement of traditional bed pillows under the body to relieve pressure and sleep systems that reduce pressure on the shoulder or other part of the body. These sleep devices have numerous problems with providing consistent comfort for the sleeper.

Recovery from a shoulder injury requires a person to endure pain, tenderness, swelling, and stiffness of the shoulder joint. The person may also experience numbness or tingling of the arm or hand where nerves have been affected in the shoulder area. Therapy to rehabilitate an injured shoulder joint may require limited or complete cessation of use of the affected arm, followed by progressive range-of-motion exercises and strength training.

Injuries or stress on any joint in the body can create difficulties for a person to perform a variety of daily activities such as work, play, sleep, and exercise. Prolonged stress or an acute injury to a joint may require medical intervention that may be costly, painful, and prolonged by additional stress to the joint during healing such as from daily activity requiring use of the joint and pressure from an improper sleep position.

The process of recovering from a shoulder joint injury may cause prolonged sleep disturbances. Traditional mattresses, pillows, recliners, and other methods and tools used for sleep may actually add pressure to an injured shoulder or cause stress or soreness to the neck, back, and opposite shoulder where certain sleep positions may be favored to help reduce pressure on the injured shoulder. For example, sleeping exclusively on the opposite shoulder may result in a sore arm and cramping of muscles. Further, sleeping in a supine position on the back may cause flattening of the lumbar curve resulting in misalignment of one or more lumbar vertebrae and/or pain where the shoulder is in contact with the bedding surface as the body sinks into the bed.

Side sleeping using the traditional sleep methods and/or tools may aggravate several medical conditions in addition to a damaged shoulder joint. For example, side sleeping may cause pain for people with asymmetrical muscular tonus in the neck and/or shoulder, a sub-luxated head of the humerus, and/or arthritis in the shoulder and/or cervical thoracic spine. Further, sleeping on the side of the body without adequate support for the head and chest may compress the shoulder into the trunk, causing muscular and ligamental tension in the shoulder girdle and neck possibly, and may inhibit normal respiration by constricting the ribs.

What is needed is an orthopedic support pillow that will alleviate musculoskeletal problems related to the neck, upper extremities, and shoulders, enabling ailing and recovering patients to rest comfortably while lying in a prone position, either on the patient's back or side while elevating a retained arm and experiencing some relief. Additionally, what is needed is an orthopedic support pillow that will provide support for an aging population suffering from arthritis in the shoulders, neck, back, and upper extremities to rest comfortably and adjust the support that the orthopedic support pillow provides over an entire range of the retained arm. More specifically, what is needed is an orthopedic support pillow that will provide support for a person with an ailing rotator cuff, to elevate such arm while reclining in a prone position with such arm elevated and supported, in a stable position, enabling such person to rest comfortably for extended periods of time.

SUMMARY

In a preferred embodiment an orthopedic support pillow is provided for use by a patient to support an arm and shoulder while the patient is resting in a generally prone position on a resting surface. In certain embodiments, the orthopedic support pillow comprises a back section for positioning and supporting the orthopedic support pillow on resting surface, the back section having a central memory foam section to adapt to the contour of the body of the patient, a head section and a rear section. The pillow further comprises a pair of side arms with features including contoured areas and a plush thickness to support the body, arms, and shoulders; and a joinder zone between the back section and side arms with shoulder support zones to engage and support the shoulders of the patient.

Alternative embodiments include the pillow as described in combination with a wedge and means to connect the wedge to the orthopedic support pillow. The wedge is configured to be placed in multiple orientations to achieve different angles of support for the pillow. A further embodiment has the described pillows including a removable, soft and washable cover.

There therapeutic pillow device described herein provides several benefits, including: (a) cradles the body; (b) allows the user to lie flat or be propped up at an angle; (c) supports the body and offers pressure relief: (d) creates a comfortable support with the center memory foam; (e) offers security due to the contoured shape; (f) benefits both "back" and "side" sleepers; (g) can be angled in a comfortable position for reading or watching television; and (h) can be manufactured on existing equipment. Other advantages and additional features of the present therapeutic pillow will be more apparent from the accompanying drawings and from the full description of the device. For one skilled in the art of therapeutic and post-surgical recovery device, it is readily understood that the features shown in the examples with this product are readily adapted to other types of therapeutic and post-operative systems and devices.

DESCRIPTION OF THE DRAWINGS

The accompanying drawings, which are incorporated in and constitute a part of this specification, illustrate certain embodiments of the therapeutic pillow disclosed herein. The drawings together with the summary and detailed description serve to explain the principles of the therapeutic pillow. It is understood, however, that the therapeutic pillow disclosed herein is not limited to only the precise arrangements and instrumentalities shown.

FIG. 1 is a top view of a therapeutic pillow according to the present disclosure.

FIG. 2 is a front view of the therapeutic pillow shown in FIG. 1.

FIG. 3 is a side view of the therapeutic pillow shown in FIG. 1.

FIG. 4 is a top partial cut-away view of the therapeutic pillow shown in FIG. 3.

FIGS. 5A-E are perspective views of the therapeutic pillow of FIG. 1 in a prone orientation on a surface, with FIGS. 5D and 5E depicting the prone pillow in use.

FIG. 7 is a side view of a wedge for use with the therapeutic pillow as shown in FIG. 3.

FIGS. 8A-8B are side views of the therapeutic pillow and the wedge of FIG. 7 shown in different orientations.

FIG. 9 is a perspective view of the wedge shown in FIG. 7 with an optional pouch.

DETAILED DESCRIPTION

Figure 6E:
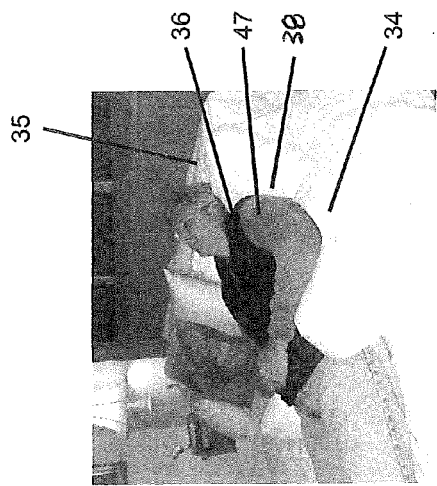
FIGS. 6A-E are perspective views of the therapeutic pillow of FIG. 1 in an upright orientation on a surface, with FIGS. 6D and 6E depicting the prone pillow in use.

The present disclosure contemplates a therapeutic pillow for aiding recovery and particularly to be used by a patient to support an arm and shoulder of the patient while resting in a generally prone position on one's side or back with the retained arm elevated and supported in a stable position. In addition, the disclosure contemplates a pillow having a malleable section of memory foam or the like and further sections of soft materials or foam surrounding the memory foam section to retain the specific shape as needed by a user/recovering patient. The pillow described herein can be used for post-operative recovery as well as for preventive use.

FIGS. 1-3 show top, front and side views of a therapeutic pillow device 31 for aiding recovery according to one disclosed embodiment. The pillow 31 includes a back section 32 with the central section 36 preferably filled with a memory foam material that conforms to the anatomy of the user. The back section 32 includes a head zone 35 where the user's head rests in use, and shoulder support zones 38 at the sides of the back section that are arranged to correspond to the location of the user's shoulders when the user's head is positioned on the head zone 35. The head zone 35 may define a slight recess or indentation 35A to comfortably receive the user's head when the pillow is used to sit upright or slightly inclined. The indentation may be aligned with the center memory foam section 36.

The pillow 31 further includes side arms 33 extending from the back section and generally in alignment with the shoulder support zones 38. The side arms have a thickness 39 adapted to support the user's arms in alignment with the shoulders, as described in more detail herein. The arms 33 and the bottom of the back section 32 are configured to rest generally flat against a surface 48, which in typical use would be the bed of the user.

The pillow 31 includes an outer shell or cover 31A sewn as a continuous body to form the back section 32 and the arms 33 as hollow components. The side arms 33 as well as the shoulder support zones 38 may include a filling of closed or open cell urethane, rubber, neoprene or equivalent, down pillow, small feather, polyester and other pillow forms, while the central section 36 of the back section 33 can include a memory foam component. In one embodiment illustrated in FIG. 4, the head zone 35 of the back section 33 can include an opening 35A to allow access to the interior of the outer shell 31A. The opening 35A may preferably incorporate a zipper or other form of closure element to close the opening. As shown in FIG. 4, a filling 32A fills the hollow interior of the pillow, including the back section and the arms. The filling 32A may be made of the materials described above for the side arms and shoulder support zones. The filling 32A may define a pocket 32B that is sized to receive a memory foam component 36A. The memory foam component 36A is sized to generally correspond to the width of the back of the user, to constitute the memory foam area 36 depicted in FIG. 2. If the user desires less rigidity in the back section 32 the memory foam component 36A can be removed from the pocket 32B.

The shell or cover 31A may fit either snugly or loosely over the filling 32A and serves a similar purpose as a conventional pillowcase. The shell may be provided in an assortment of colors and patterns and may be re-useable or disposable. The shell may be formed of an allergy free woven or nonwoven material. The surface of the shell may include patterns, indentations or grooves to enhance the comfort of the pillow. The memory foam component 36A may be formed of polyurethane but may also be of other new composite materials that compress to take the contour of the body of the patient and provide added support as compared with standard foam or filling that "springs back" and has no residual contouring properties. Traditionally the memory foam is a lower-density memory foam that is pressure-sensitive and molds quickly to the shape of a body pressing against it, returning to its original shape once the pressure is removed. A memory foam mattress is usually denser than other foam devices, making it both more supportive, and heavier. Cell structures vary from very open, to almost closed cell. The tighter the cell structure, the less airflow through the foam. "Breathable" visco-elastic foam will have a more open cell structure, allowing higher airflow, better recovery, and lower odor retention at packaging. The properties of a device depend upon its height, density, and type. While the term "foam" has been used to describe the present invention, the present invention should not be limited to "foam" since other materials, either natural or synthetic, may be used without departing from the scope of the invention.

The head region 35 of the back section 32 may be provided with one or more handles 37 that can be gasped by the user to lift and carry the pillow 31. The handles may preferably be formed of the same material as the cover 31A so that the handles blend into the appearance of the pillow. Thus, in one embodiment the handles are in the form of fabric strips sewn to the cover and sized to receive the user's fingers to grasp the handles.

In one aspect of the pillow 31, the arms 33 are each provided with one or more indentations or reduced width regions 34. The regions 34 operate as hinges that facilitate inward or outward movement of the arms, such as accommodate the girth of the user's torso. The indentations 34 immediately adjacent the base of the back section 32 also operate as hinges to bend the back section upward to an upright position. The indentations or regions 34 may also provide comfortable resting places for a user's arms when the user is resting or sleeping on his/her side. The indentations 34 thus provide areas of decreased lateral rigidity of the arms 33 while the portions of the arms between indentations retain sufficient lateral rigidity to maintain the generally linear configuration of the arms.

Figure 6D:
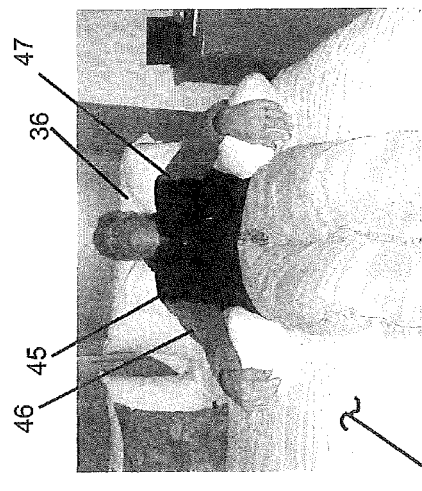
Figure 6C:
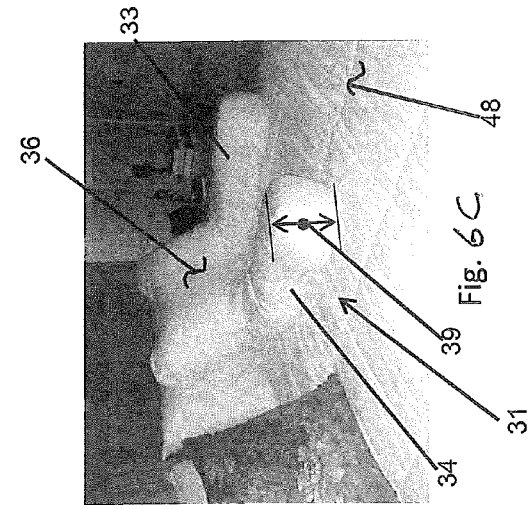
Figure 6B:
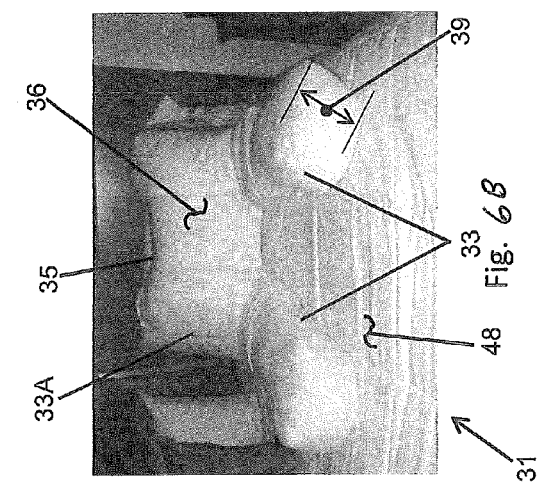
Figure 6A:
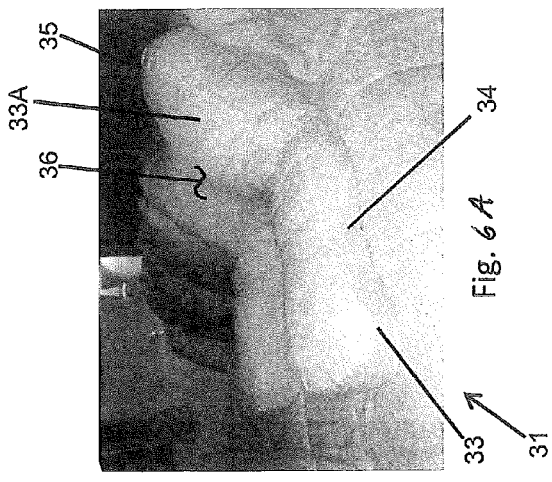

FIGS. 5A-5E and 6A-6E depict two modes of orientation for the pillow 31. In FIGS. 5A-5E the pillow lays flat on the surface 48 or bed. A user may use the pillow to sleep prone, as reflected in FIG. 5D, or on his/her side, as shown in FIG. 5E. In FIGS. 6A-6E the pillow is arranged with the back section 32 propped up against other pillows, a headboard or a wall. FIGS. 6D and 6E show a user 45 positioned with his/her arms 46 extending along the arms 33 of the pillow and his/her shoulders 47 aligned with the shoulder support zones 38. In another aspect, the central memory section 36 contours to the body of the patient 45 and allows the shoulder 47 to be lightly supported by the remaining pillow in the shoulder support zone 38 with little or no aggravation from the body weight of the patient.

In another embodiment, the pillow 31 may be provided with a support wedge 50, as shown in FIG. 3. The wedge 50 is preferably removable attachable to the pillow 31 at an attachment zone 51. The attachment zone may include a hook-and-loop fastener 52 (i.e., by VELCRO® strips) or other suitable means for temporarily attaching the pillow and wedge together. The wedge 50 may be configured to have a cross-section in the form of a right triangle with sides 54, 55 and 56 all having different lengths. Each length may have a fastener element 52 as described above so that the wedge may be attached to the pillow in different orientations. As shown in FIG. 3, the wedge 50 may be attached with side 54 abutting the pillow 31 so that the back section 32 is essentially completely upright (i.e., at 90°). Alternatively, the wedge may be positioned with the long side 56 abutting the pillow, as shown in FIG. 8A, or with the side 56 in contact with the pillow, as shown in FIG. 8B. It can be appreciated that the angle of the head section 32 is a function of which side of the wedge 50 is attached to the pillow. The wedge 50 thus allows the user to find an orientation that is most comfortable.

As shown in FIG. 9, the wedge 50 may optionally include one or more pouches 58 affixed to one or more of the sides, such as side 54 shown in the drawing. The pouch may be sized and configured to carry a book or magazines for ready access by the user. It is understood that the wedge 50 may be provided with a removable cover formed of the same material as the pillow cover. In this case, the cover fits over a foam material shaped to form the wedge 50. The foam material may be the same filling as the arms of the pillow.

In one preferred use the therapeutic pillow is provided for aiding recovery and particularly for use by a patient to support an arm and shoulder while the patient is resting in a generally prone position or slightly inclined on a resting surface. A beneficial focus is for people recovering from shoulder, neck, arm, or back surgery but the pillow is equally useful for people who have injuries or are suffering discomfort in any of these related areas. People suffering from acid reflux or minor digestive issues can benefit when the pillow is propped up at an angle. The shape and size of the pillow offers comfort and security to people who spend a large amount of time in bed due to illness or age, such as in nursing homes, hospice care or extended care facilities. The extended arms offer stability and support for pressure relief and are ideal for while relaxing in bed, watching television, and reading.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A therapeutic pillow for use by a user to support an arm and shoulder while the user is resting in a generally prone position on a resting surface, the pillow comprising:
    a back section including a central section and shoulder support zones flanking the central section;
    a pair of side arms extending from the back section at the shoulder support zones,
    wherein the central section includes a memory foam component, and
    wherein the shoulder support zones and pair of side arms include a non-memory foam filling different from said memory foam component, and
    further wherein the back section and pair of arms are configured to rest on a surface with the user resting on the back section with the arms flanking the torso of the user,
    wherein the arms are provided with regions of reduced lateral rigidity to permit lateral movement of the arms at said regions.

2. The pillow of claim 1, wherein each arm includes a region of reduced lateral rigidity at the intersection with the back section.

3. The pillow of claim 1, further comprising a single cover configured to fit over the back section and the pair of side arms.

4. The pillow of claim 1, wherein the head section includes an indentation at an upper surface thereof and aligned with central section, said indentation configured to receive the head of the user.

5. The pillow of claim 1, further comprising at least one handle affixed to the head section of the pillow and configured to be manually grasped to carry the pillow.

6. A therapeutic pillow for use by a user to support an arm and shoulder while the user is resting in a generally prone position on a resting surface, the pillow comprising:
    a back section including a central section and shoulder support zones flanking the central section;
    a pair of side arms extending from the back section at the shoulder support zones,
    wherein the central section includes a memory foam component, and
    wherein the shoulder support zones and pair of side arms include a non-memory foam filling different from said memory foam component, and
    further wherein the back section and pair of arms are configured to rest on a surface with the user resting on the back section with the arms flanking the torso of the user,
    wherein the filling defines a pocket in said head section and the memory foam component is sized to be received within said pocket.

7. The pillow of claim 6, wherein each arm includes a region of reduced lateral rigidity at the intersection with the back section.

8. The pillow of claim 6, further comprising a single cover configured to fit over the back section and the pair of side arms.

9. The pillow of claim 6, wherein the head section includes an indentation at an upper surface thereof and aligned with central section, said indentation configured to receive the head of the user.

10. A therapeutic pillow for use by a user to support an arm and shoulder while the user is resting in a generally prone position on a resting surface, the pillow comprising:
    a back section including a central section and shoulder support zones flanking the central section, wherein the central section includes a memory foam component and the shoulder support zones and pair of side arms include a non-memory foam filling different from said memory foam component;
    a pair of side arms extending from the back section at the shoulder support zones;
    a wedge component; and
    a removable attachment element between the wedge component and the back section of the pillow,
    wherein the wedge component is configured to support the back section at an angle to the resting surface, and
    further wherein the back section and pair of arms are configured to rest on a surface with the user resting on the back section with the arms flanking the torso of the user.

11. The pillow of claim 10, wherein said wedge component has a right triangular cross-section.

12. The pillow of claim 11, wherein said the wedge component includes three sides of different length relative to each other.

13. The pillow of claim 12, wherein each of the three sides includes a removable attachment element for removable attachment to the back section of the pillow.

* * * * *